US008581587B2

(12) United States Patent
Walsh et al.

(10) Patent No.: US 8,581,587 B2
(45) Date of Patent: Nov. 12, 2013

(54) SNMR PULSE SEQUENCE PHASE CYCLING

(75) Inventors: David O. Walsh, Mukilteo, WA (US);
Elliot D. Grunewald, Seattle, WA (US)

(73) Assignee: Vista Clara Inc., Mukilteo, WA (US)

( * ) Notice: Subject to any disclaimer, the term of this patent is extended or adjusted under 35 U.S.C. 154(b) by 282 days.

(21) Appl. No.: 13/104,721

(22) Filed: May 10, 2011

(65) Prior Publication Data

US 2012/0286779 A1    Nov. 15, 2012

(51) Int. Cl.
*G01V 3/00*    (2006.01)

(52) U.S. Cl.
USPC .......................................... 324/318; 324/309

(58) Field of Classification Search
USPC .......................... 324/300–322; 600/407–445
See application file for complete search history.

(56) References Cited

U.S. PATENT DOCUMENTS

| | | | |
|---|---|---|---|
| 3,019,383 A | 1/1962 | Varian | |
| 5,415,163 A * | 5/1995 | Harms et al. | 600/410 |
| 6,774,628 B2 * | 8/2004 | Ganesan | 324/303 |
| 6,956,370 B2 * | 10/2005 | Heidler | 324/303 |
| 7,466,128 B2 * | 12/2008 | Walsh | 324/309 |

OTHER PUBLICATIONS

O.A. Shushakov, "Surface NMR measurements of proton relaxation times in medium to coarse-grained sand aquifer"; Magnetic Resonance Imaging, vol. 16, No. 7/8, 1996.
A. Legchenko, J.-M. Baltassat, A. Bobachev, C. Marin, H. Robain, and J.-M. Vouillamoz, "Magnetic resonance sounding applied to aquifer Characterization"; Ground Water, vol. 42, No. 3, Jun. 2004.
Legchenko et al, "Application of the magnetic resonance sounding method to the investigation of aquifers in the presence of magnetic materials"; Geophysics, vol. 75, No. 6, Nov.-Dec. 2010.
M. Hertrich, "Imaging of groundwater with nuclear magnetic resonance"; Progress in Nuclear Magnetic Resonance Spectroscopy, vol. 53, 2008.
Shushakov and Fomenko, "Surface-NMR Relaxation and Echo of Aquifers in Geomagnetic Field,"; Appl. Nagn. Reson., vol. 25, pp. 599-610, 2004.
J.O. Walbrecker, M. Hertrich, and A.G. Green, "Improving surface-NMR estimates of nuclear-spin relaxation (T1)"; 16th European Meeting of Environmental and Engineering Geophysics, Sep. 2010.
D.E. Demco, P. Van Hecke, and J.S. Waugh, "Phase-shifted pulse sequences for measurement of spin-Lattice relaxation in complex systems"; Journal of Magnetic Resonance, vol. 16, 1974.
Bendall and Gordon, "Depth and Refocusing Pulses Designed for Multipulse NMR with Surface Coils"; Journal of Magnetic Resonance, vol. 53 (1983).
D.O. Walsh, E. Grunewald. P. Turner, A. Hinnell, and P. Ferre, "Practical limitations and applications of short dead time surface NMR"; Near Surface Geophysics, vol. 9, 2011.
S. Meiboom and D. Gill, "Modified Spin-Echo Method for easuring Nuclear Relaxation Times"; The Review of Scientific Instruments, vol. 29, Aug. 1958.

* cited by examiner

*Primary Examiner* — Brij Shrivastav
(74) *Attorney, Agent, or Firm* — Jensen & Puntigam, PS

(57) ABSTRACT

Technologies applicable to SNMR pulse sequence phase cycling are disclosed, including SNMR acquisition apparatus and methods, SNMR processing apparatus and methods, and combinations thereof. SNMR acquisition may include transmitting two or more SNMR pulse sequences and applying a phase shift to a pulse in at least one of the pulse sequences, according to any of a variety of phase cycling techniques. SNMR processing may include combining SNMR from a plurality of pulse sequences comprising pulses of different phases, so that desired signals are preserved and undesired signals are canceled.

20 Claims, 4 Drawing Sheets

SNMR PULSE SEQUENCE PHASE CYCLING

STATEMENT OF GOVERNMENT SUPPORT

This invention was made with Government support under Agreement No. DE-FG02-08ER84979 awarded by the Department of Energy. The Government has certain rights in this invention.

BACKGROUND

Nuclear Magnetic Resonance (NMR) systems have been in use for many years and can be used to provide imaging and/or analysis of a sample being tested. For example, U.S. Pat. No. 6,160,398, U.S. Pat. No. 7,466,128, U.S. patent application Ser. No. 12/672,503, and U.S. patent application Ser. No. 12/914,138 describe a variety of NMR technologies, and are incorporated herein by reference. Various different types of NMR include medical NMR, often referred to as Magnetic Resonance Imaging (MRI), and Surface NMR (SNMR), which provides geophysical techniques for detecting subsurface liquids in the earth's crust. While there is some overlap in the technologies that may be applied in MRI and SNMR, the samples being measured and the environments in which measurements are performed are different, leading to many differences in the technologies applied.

In practice, the signals recorded by SNMR instruments can contain a combination of both "desired" and "undesired" signals. The desired signals are those particular coherent signals emitted by subsurface liquids that can be analyzed to determine the properties of the subsurface. The undesired signals are any coherent signals that complicate this analysis and may include signals from non-NMR sources as well as interfering signals from NMR sources. Existing SNMR detection techniques are generally useful for detecting desired signals in a background of white Gaussian noise. Existing SNMR detection techniques are not as useful for detecting desired NMR signals in the presence of undesired signals and other undesired interference processes.

SUMMARY

Technologies applicable to SNMR pulse sequence phase cycling are disclosed, including SNMR acquisition apparatus and methods, SNMR processing apparatus and methods, and combinations thereof. Example SNMR acquisition methods include arranging one or more induction coils on the surface of the Earth, transmitting two or more electrical current pulse sequences on the induction coils, each pulse sequence comprising one or more oscillating electrical current pulses, and applying a phase shift to a pulse in at least one of the pulse sequences relative to a pulse in another of the pulse sequences. The phase shift may be applied according to a variety of SNMR pulse sequence phase cycling techniques disclosed herein.

SNMR acquisition methods may be combined with SNMR processing methods in some embodiments. For example, the disclosed SNMR methods may extend to detecting signals on the induction coils after and/or during each of the electrical current pulse sequences, and linearly combining detected signal data corresponding to separate electrical current pulse sequences to produce combined signal data in which one or more detected signal components are preserved and one or more different detected signal components are reduced or cancelled. The preserved signal components may comprise NMR signal data, and the reduced or cancelled signal components comprise undesired NMR signal data and/or non-NMR signal data. Alternatively, the preserved signal components may comprise undesired NMR signal data and/or non-NMR signal data, and the reduced or cancelled signal components comprise NMR signal data.

Example SNMR acquisition systems may comprise systems configured to produce NMR in underground liquids, including a SNMR phase cycling computer comprising a processor and memory, the SNMR phase cycling computer comprising one or more SNMR phase cycling acquisition modules. The SNMR acquisition modules may be configured to control transmitting of two or more electrical current pulse sequences on induction coils arrangeable on or above the surface of the Earth, each transmitted pulse sequence comprising one or more oscillating electrical current pulses. The SNMR acquisition modules may be configured to apply a phase shift to a pulse in at least one of the transmitted pulse sequences relative to a pulse in another of the transmitted pulse sequences. The phase shift may be applied according to a variety of SNMR pulse sequence phase cycling techniques disclosed herein. Also, SNMR acquisition systems may comprise a variety of additional components such as oscillating waveform generator devices, power amplifier(s), one or more transmit switches, one or more induction coils, one or more receive switches, one or more preamplifiers, and an Analog to Digital (A/D) converter device.

Example SNMR processing methods include coherently combining detected NMR signal data, such as NMR signal data detected from an underground liquid, and including NMR signal data from two or more separate electrical current pulse sequences, each of the pulse sequences comprising one or more oscillating electrical current pulses, and wherein the phase of a pulse in at least one of the pulse sequences is shifted relative to a pulse in another of the pulse sequences. SNMR processing methods may further include recording a combined NMR signal in which a desired Free Induction Decay (FID) signal is preserved, and undesired signals that are coherent with the timing of the electrical current pulse sequences but independent of the phases of the oscillating electrical current pulses are cancelled.

Example SNMR processing systems may comprise a computer equipped with a processor and memory, and one or more SNMR phase cycled signal data processing modules configured to coherently combine detected NMR signal data. The detected NMR signal data may include, for example, data detected from an underground liquid, and including NMR signal data from two or more separate electrical current pulse sequences, each of the pulse sequences comprising one or more oscillating electrical current pulses, and wherein the phase of a pulse in at least one of the pulse sequences is shifted relative to a pulse in another of the pulse sequences. The SNMR processing modules may be further configured to record combined NMR signal data, in which a desired FID signal is preserved, and undesired signals that are coherent with the timing of the electrical current pulse sequences but independent of the phases of the oscillating electrical current pulses are cancelled.

Further aspects and variations are discussed in detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein.

DETAILED DESCRIPTION

Figure 1:
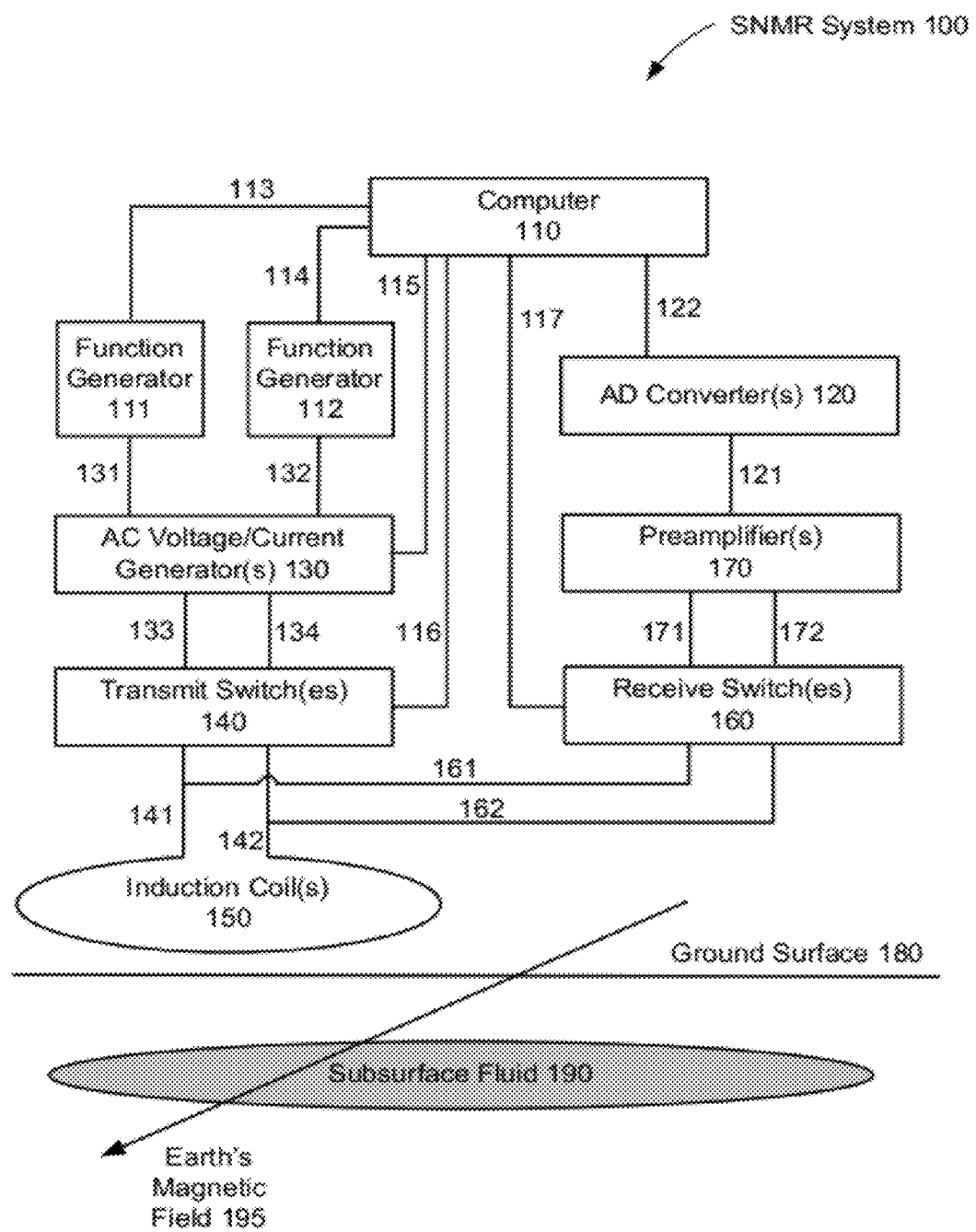
FIG. 1 illustrates aspects of an example SNMR system configured to perform SNMR pulse sequence phase cycling.

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies applicable to SNMR pulse sequence phase cycling may include, inter alia, SNMR acquisition apparatus and methods, SNMR processing apparatus and methods, and combinations thereof. SNMR acquisition according to this disclosure may include transmitting two or more SNMR pulse sequences and applying a phase shift to a pulse in at least one of the pulse sequences relative to a pulse in another of the pulse sequences. The phase shift may be applied according to a variety of phase cycling techniques. SNMR processing may include combining NMR signals resulting from a plurality of pulse sequences comprising pulses of different phases, in such a manner as to preserve desired signals and cancel undesired signals.

FIG. 1 illustrates aspects of an example SNMR system 100 configured to perform SNMR pulse sequence phase cycling. The example SNMR system 100 includes a computer 110, function generators 111, 112, AC voltage/current generator(s) 130, transmit switch(es) 140, induction coil(s) 150, receive switch(es) 160, preamplifier(s) 170, and Analog to Digital (AD) converter(s) 120. The induction coil(s) 150 are illustrated over a ground surface 180. A subsurface fluid 190 is illustrated beneath the ground surface 180. Earth's magnetic field 195 exists over and under the ground surface 180 and within the subsurface fluid 190.

In FIG. 1, the computer 110 is coupled to function generators 111, 112 by connections 113 and 114, respectively. The computer 110 is also coupled to AC voltage/current generator(s) 130 by connection 115, to transmit switch(es) 140 by connection 116, to receive switch(es) 160 by connection 117, and to AD converter(s) 120 by connection 122. Furthermore, function generators 111, 112 are coupled to AC voltage/current generator(s) 130 by connections 131 and 132, respectively. AC voltage/current generator(s) 130 are coupled to transmit switch(es) 140 by connections 133 and 134. Transmit switch(es) 140 are coupled to both ends of the induction coil(s) 141 and 142. The ends of the induction coil(s) 141 and 142 are coupled to receive switch(es) 160 by connections 161 and 162, respectively. Receive switch(es) 160 are coupled to preamplifier(s) 170 by connections 171 and 172. Preamplifier(s) 170 are coupled to AD converter(s) 120 by connection 121. AD converter(s) 120 are coupled to AD converter(s) 120 by connection 121.

In general, with regard to FIG. 1, the SNMR system 100 may be configured to produce electrical current pulse sequences on the induction coils 150. Each electrical current pulse sequence may comprise one or more oscillating electrical current pulses. When a pulse sequence comprises more than one pulse, the pulses may be separated by a pulse separation time. Also, pulse sequences may be separated by a pulse sequence separation time.

The computer 110 may be configured to produce a pulse by selecting a pulse phase, and activating the AC voltage/current generator(s) 130. The computer 110 may be configured to select a pulse phase for example by activating a function generator 111 or 112 corresponding to a desired pulse phase, so that the selected function generator 111 or 112 provides an input pulse phase to the AC voltage/current generator(s) 130, which is then amplified by the AC voltage/current generator(s) 130 to produce a corresponding pulse on the induction coil(s) 150. The computer 110 may also optionally be configured to close one or more transmit switch(es) 140 when activating the AC voltage/current generator(s) 130, and open the transmit switch(es) 140 after activating the AC voltage/current generator(s) 130.

The computer 110 may be configured to produce a pulse sequence by producing a first pulse, then if additional pulses are included in the sequence, waiting for a predetermined pulse separation time, and then producing a next pulse, and repeating until the pulse sequence is complete. The computer 110 may be configured to produce two or more pulse sequences by producing a first pulse sequence, then waiting for a predetermined pulse sequence separation time, then producing a next pulse sequence, and repeating until a desired number of pulse sequences are complete.

The SNMR system 100 may also be configured to receive and record NMR signal data received via the induction coil(s) 150. The SNMR system 100 may be configured to receive and record NMR signal data after one or more pulses within a pulse sequence, and/or after completion of a pulse sequence. In some embodiments, the computer 110 may be configured to close the receive switch(es) 160 after a pulse. The preamplifier(s) 170 amplify desired and undesired signals received via induction coil(s) 150. The AD converter(s) 120 convert the received and amplified signals to digital NMR signal data, e.g. by sampling received signals at a desired sampling rate, and the computer 110 or other device equipped with storage media may be configured to store the digital NMR signal data.

In some embodiments, the computer 110 may be configured to process detected NMR signal data, e.g., to combine NMR signal data received and recorded after one or more pulses within a pulse sequence, and/or received and recorded after completion of pulse sequences, in such a way that preserves desired NMR signal data and cancels undesired NMR signal data. It will be appreciated that while the computer 110 may be configured to perform SNMR processing, in some embodiments SNMR acquisition and SNMR processing may be performed separately, e.g., by first performing SNMR acquisition with a SNMR system 100, then processing acquired SNMR data at a later time and/or with a different computing device.

In some embodiments, computer 110 may be programmed with software that controls the generation of pulse sequences and the acquisition of data. A set of data acquisition devices may comprise devices configured generate the control signals for the pulse sequences, such as function generators 111, 112, and AD converter(s) 120 that receive, convert and/or record SNMR signals. The AC voltage/current generator(s) 130 may be configured to generate one or more current pulses in the induction coil(s) 150 in a transmit mode, to induce a coherent precession of NMR spins in the subsurface fluid 190. Optional transmit switch(es) 140 may be configured to isolate transmitter noise from the receive circuitry during a receive mode. Induction coil(s) 150 may be arranged on or above the surface of the Earth 180, and may be configured to cause a coherent precession of spins in the subsurface fluid 190 in the Earth's magnetic field 195 and also to detect the NMR magnetic fields generated by the coherent precession of spins in the subsurface fluid 195. Optional receive switch(es) 160 may be configured to isolate the receive preamplifier(s) 170 from the potentially large voltage on the induction coil(s) 150 during transmit mode. Optional preamplifier(s) 170 may be configured to amplify the detected NMR signals prior to digitization by the AD converter(s) 120. The optional transmit switch(es) 140 and receive switch(es) 160 may comprise active devices such as relays, and/or passive devices such as diodes. Optional tuning capacitors, not shown in FIG. 1, may be used in the transmit mode to increase the transmitted current in the induction coil(s) 150, and/or in receive mode to increase the amplitude of the NMR signal voltage across the terminals of the induction coil(s) 150.

In some embodiments, induction coil(s) 150 may comprise an array of coils comprising one or more transmit coils, one or more receive coils, and/or one or more combination transmit and receive coils. For example, induction coil(s) 150 may comprise one transmit coil and multiple receive coils. Induction coil(s) 150 may comprise one combination transmit and receive coil, and multiple receive coils. Induction coil(s) 150 may comprise multiple combination transmit and receive coils. These and other multicoil arrangements may be configured in some embodiments as will be appreciated. Multicoil arrangements are useful for localization of subsurface fluids 190, as described for example in U.S. Pat. No. 7,466,128, which is incorporated by reference.

Any combination of hardware and software that enables the acquisition and processing of NMR signals from subsurface liquids in the Earth's magnetic field is suitable to implement embodiments of this disclosure. An architecture to implement the disclosed methods could comprise, for example, elements illustrated in FIG. 1, such as an AC voltage and current generator 130, a digital control system implemented at least in part by computer 110, a transmit switching circuit including transmit switch(es) 140, a receive switching circuit including receive switch(es) 160, a multi-channel receive circuit including, e.g., a plurality of induction coils 150, preamplifier(s) 170, a digital acquisition system including AD converter(s) 120, a digital storage device which may be implemented within computer 110 or other digital storage device, and a digital computer 110 equipped with pulse sequence control software and/or SNMR processing software. The switching circuits may transition a system such as 100 between a transmit-mode, when the coil(s) 150 are connected to the transmit circuit, and receive-mode when the coil(s) 150 are connected to the receive circuit. In a single acquisition sequence, the transmit circuit directs an AC current pulse or pulses with controlled amplitude and phase (alternating at the Larmor frequency) through the induction coil(s) 150 in short succession. As quickly as possible after a given transmit pulse, and before the next pulse, the switching circuits may transfer the induction coil(s) 150 into a single- or multi-channel receive circuit. The data acquisition system may then record the voltages on the receive circuit (including the surface coil(s) 150), and may record this received NMR signal data following the transmit pulse on the digital storage device. To form a complete cycled set, an acquisition sequence may be repeated one or more times, changing the phase of one or more transmit pulses between each acquisition sequence. After a complete cycled set corresponding to a NMR measurement is acquired, the signals recorded from each acquisition sequence may be linearly combined through digital processing.

In general, a SNMR measurement may be collected by transmitting one or more pulses of alternating current through a wire loop on the Earth's surface. The alternating current may be tuned to the Larmor frequency of hydrogen nuclei, and may generate a magnetic field in the subsurface beneath the coil(s) alternating at the Larmor frequency. The alternating magnetic field radiates into the Earth and modifies the nuclear magnetization state of hydrogen present in fluids at depth. At equilibrium, the net nuclear magnetization is aligned with Earth's background magnetic field along the so-called longitudinal axis. The transmitted alternating magnetic field perturbs the magnetization from this equilibrium alignment so that some component of the nuclear magnetization rotates into the transverse "xy" plane. Once rotated from equilibrium, the magnetization relaxes over time back to the equilibrium state over time, decaying from the transverse plane and re-growing along the longitudinal axis. The rotation of the magnetization by the transmitted pulse(s) and subsequent relaxation to equilibrium are described by the phenomenological Bloch equations. The evolution of the magnetization under the Bloch equations depends on several variables including the amplitude of the transmitted field, the duration and timing of the transmitted field, the phase of the transmitted field, the longitudinal relaxation time $T_1$, FID relaxation rate $T_2^*$, and/or the spin-spin relaxation time $T_2$ of the hydrogen nuclei under investigation.

An NMR signal is generated by the presence of coherent transverse magnetization following a transmit pulse. The transverse magnetization generates a magnetic field, which oscillates at the Larmor frequency, and generally has a phase related to the phase of one or more of the transmitted pulses. The SNMR instrumentation records the NMR signal by monitoring the voltage on the surface loop. Identical measurements may be repeated to improve signal to noise; measurements using varied transmit currents may be used to modulate the contribution of signals from groundwater at different depths. Spatial inversion techniques may be used to isolate NMR signal contributions from different depth ranges or different locations in a 2D or 3D model of the subsurface, as described in U.S. Pat. No. 7,466,128.

Measurement schemes with one or more excitation pulses may be used to probe different types of NMR responses and properties. In a single pulse measurement, a single pulse rotates a component of the magnetization into the transverse plane. The signal produced as this coherent transverse magnetization relaxes to equilibrium is called the Free Induction Decay (FID) signal. In the single pulse sequence, the pulse sequence is repeated only after a delay period that is sufficiently long to allow the longitudinal relaxation process of liquid hydrogen samples in the subsurface to relax to their steady state. The FID signal can be used to determine the quantity of subsurface water content and the effective transverse relaxation time $T_2^*$. Double pulse sequences may be used to probe other relaxation times, such as $T_1$ and/or $T_2$. The first pulse rotates a component of the magnetization into the transverse plane; a second pulse transmitted after a controlled delay further modifies and rotates the magnetization state so that the recorded signal following the second pulse contains information about the decay times $T_1$ and/or $T_2$.

For single-pulse measurements, the desired signal is the FID signal, which is the only NMR signal contained in the measurement. Undesired coherent signals in a single-pulse measurement may be associated with non-NMR processes including instrumentation artifacts as well as the inductive response of the conductive earth following the termination of the transmit pulse. Multiple-pulse measurements can also contain undesired NMR signals. In addition to non-NMR artifacts, multiple-pulse measurement sequences can produce multiple NMR signals, some of which are undesired due to the fact that they complicate accurate extraction of the decay times of interest T1 and/or T2.

Embodiments of the present disclosure may take advantage of the fact that the phase of a certain coherent signals is dependent upon specific controllable parameters, while the phase of other coherent signals is independent of these parameters. Specifically for SNMR measurements, the phase of certain coherent signals will be linearly correlated with the phase of one or more transmit pulses, while the phase of other coherent signals may be constant, negatively correlated, or otherwise independent of the transmit pulse. As an example, in FIG. 4, the top left graph illustrates a transmitted pulse P(t) that may produce signals illustrated in the bottom left graph, including one signal SA(t) that has the same phase as P(t), and a second signal SB(t) that has a constant phase independent of P(t). Introducing a 180 degree phase shift to P(t), as shown at top right, will likewise introduce a 180 degree phase shift to SA(t), as shown bottom middle, but will not change the phase of SB(t). Thus, if between a pair of independent measurements, the phase of P(t) is shifted by 180 degrees, the phase of SA(t) will also be shifted by 180 degrees while the phase of SB(t) will be constant. By subtracting this pair of phase-cycled signals, it is then possible to preserve SA(t) while eliminating SB(t), as show bottom right. Thus by phase-cycling one transmit pulse, it is possible to isolate signals that are phase-correlated with that pulse from those signal which are not phase-correlated with that particular pulse.

In some embodiments, the phase of each transmitted pulse may be defined relative to the phase of an un-modulated reference sinusoid at the selected transmitting frequency, wherein the phase of the reference sinusoid does not change with respect to the timing of various applied pulse sequences associated with a measurement. For example, one may define a reference sinusoid such that it has a phase of 0 degrees such that the reference sinusoid has a zero crossing at time t=0. The absolute phase is unimportant, as this can always be removed in post processing. The important relationship is the relative phases of the various pulses in the applied pulse sequences.

The phase of a transmitted pulse may be controlled and changed in a number of ways. For example, if the transmitted pulses are generated using local oscillators, then the transmitted phase may be controlled by using multiple oscillators with different phases, for example, two oscillators such as function generator 111 and 112, one with a phase of 0 degrees and one with a phase of 180 degrees, and switching between the different oscillators to produce different pulses. In another example, if the transmitted pulses are generated by a computer-controlled digital or analog output device, then the phase of each transmitted pulse may be controlled by software.

Figure 4:
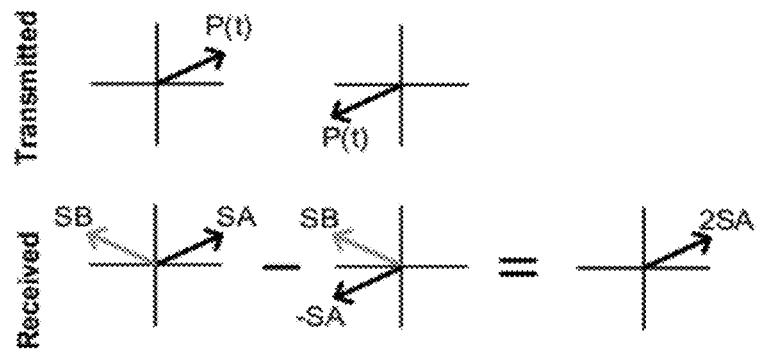
FIG. 4 illustrates example transmitted pulses, in the top graphs, that produce signals illustrated in the bottom graphs, which signals may received, recorded and combined as shown.

Instrument switching artifacts are one type of undesired signal that may interfere with SNMR measurements. Embodiments of the present disclosure may also be employed remove undesired switching artifacts that are coherent, repeatable, and have no phase dependence on the transmit pulse. The example in FIG. 4 describes the application of the present disclosure to preserve a desired NMR signal while suppressing an undesired instrumentation artifact. In FIG. 4, the desired signal, denoted SA, is an NMR signal that has a phase linearly correlated with transmit pulse. In FIG. 4 the undesired signal, denoted SB, is a repeatable undesired instrumentation artifact signal whose phase is uncorrelated with the transmitted pulse. The transverse magnetization signal resulting from the rotation of longitudinal magnetization into the transverse plane by a transmit pulse is correlated in phase with the phase of the transmit pulse; under non-resonance conditions the phase of this signal is the same as that of the transmit pulse. Thus cycling the phase of any transmitted pulse in a pair of measurements will also cycle the phase of the transverse magnetization rotated from the longitudinal axis by that pulse. On the other hand, coherent and repeatable switching artifacts that do not change phase with the transmit pulse, will maintain constant phase between the measurement pairs. Using a pair of measurements in which the transmit pulse is cycled between ø and ø+180°, provides two recorded signals pairs that can be subtracted to isolate switching artifacts from the desired NMR signal.

Figure 2:
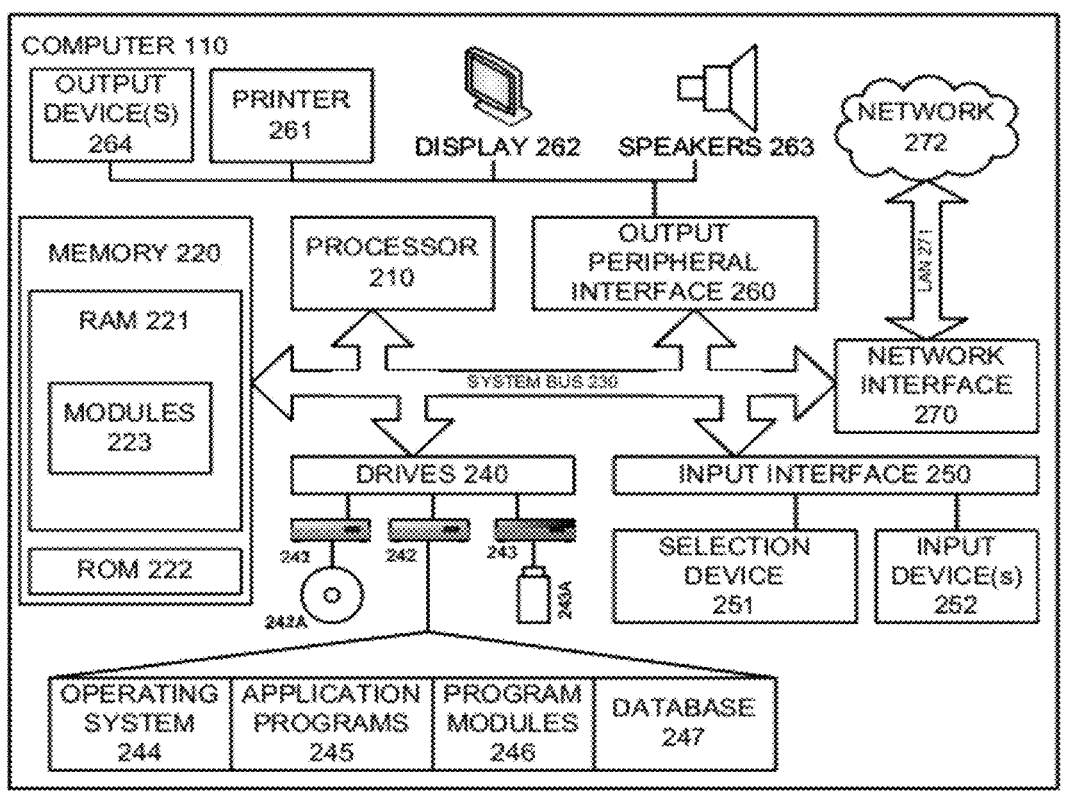
FIG. 2 is a block diagram illustrating an example computer configured to perform SNMR pulse sequence phase cycling.

FIG. 2 is a block diagram illustrating an example computer 110 configured to perform SNMR pulse sequence phase cycling. As discussed in connection with FIG. 1, the computer 110 may be configured to produce pulse sequences, to receive and record resulting NMR signal data, and/or to perform processing of NMR signal data.

Computing device 110 may include for example a processor 210, memory 220, system bus 230, one or more drives 240, user input interface 250, output peripheral interface 260, and network interface 270. Drives 240 may include, for example, a compact disk drive 241 which accepts an optical disk 241A, a so-called hard drive 242, which may employ any of a diverse range of computer readable media, and a flash drive 243 which may employ for example a Universal Serial Bus (USB) type interface to access a flash memory 243A. Drives may further include network drives and virtual drives (not shown) accessed via the network interface 270.

The drives 240 and their associated computer storage media provide storage of computer readable instructions, data structures, program modules and other data for the computer system 110. For example, a hard drive 242 may include an operating system 244, application programs 245, program modules 246, and database 247. Software aspects of the technologies described herein may be implemented, in some embodiments, as computer readable instructions stored on any of the drives 240 or on network 272, which instructions may be loaded into memory 220, for example as modules 223, and executed by processor 210.

Computer system 110 may further include a wired or wireless input interface 250 through which selection devices 251 and input devices 252 may interact with the other elements of the system 110. Selection devices 251 and input devices 252 can be connected to the input interface 250 which is in turn coupled to the system bus 230, allowing devices 251 and 252 to interact with processor 210 and the other elements of the system 110. Interface and bus structures that may be utilized to implement 250 may include for example a Peripheral Component Interconnect (PCI) type interface, parallel port, game port and a wired or wireless Universal Serial Bus (USB) interface.

Selection devices 251 such as a mouse, trackball, touch screen, or touch pad allow a user to select among desired options and/or data views that may be output by the computer 110, for example via the display 262. Input devices 252 can include any devices through which commands and data may be introduced to the computer 110. For example, in some embodiments the AD converter(s) 120 may be coupled to the computer 110 as an input device 252, and data received from the AD converter(s) 120 may be stored in drives 240. Other example input devices 252 include a keyboard, an electronic digitizer, a microphone, a joystick, game pad, satellite dish, scanner, media player, mobile device, or the like.

Computer system 110 may also include an output peripheral interface 260 which allows the processor 210 and other devices coupled to bus 230 to interact with output devices such as the function generators 111, 112, the AC voltage/current generator(s) 130, the transmit switches 140, the receive switches 160, and optionally a Digital to Analog (DA) converter as discussed further herein. Other example output devices include printer 261, display 262, and speakers 263. Interface and bus structures that may be utilized to implement 260 include those structures that can be used to implement the input interface 250. It should also be understood that many devices are capable of supplying input as well as receiving output, and input interface 250 and output interface 260 may be dual purpose or support two-way communication between components connected to the bus 230 as necessary.

Computing system 110 may operate in a networked environment using logical connections to one or more computers. By way of example, FIG. 2 shows a LAN 271 connection to a network 272. A remote computer may also be connected to network 271. The remote computer may be a personal computer, a server, a router, a network PC, a peer device or other common network node, and can include many or all of the elements described above relative to computing system 110. Networking environments are commonplace in offices, enterprise-wide area networks (WAN), local area networks (LAN), intranets and the Internet.

When used in a LAN or WLAN networking environment, computing system 110 is connected to the LAN through a network interface 270 or an adapter. When used in a WAN networking environment, computing system 110 typically includes a modem or other means for establishing communications over the WAN, such as the Internet or network 272. It will be appreciated that other means of establishing a communications link between computers may be used.

In some embodiments, computing system 110 may include modules 246 and/or 223 comprising, inter alia, one or more SNMR phase cycling acquisition modules, and one or more SNMR phase cycled signal data processing modules, which may be referred to herein as SNMR acquisition modules and SNMR processing modules, respectively.

The SNMR acquisition modules may be configured to control transmitting of two or more electrical current pulse sequences on induction coils arrangeable on or above the surface of the Earth. For example, the SNMR acquisition modules may be configured to control the phases of pulses with each pulse sequence, the time between pulses, the number of pulses, the number of pulse sequences, and the time between pulse sequences. The SNMR acquisition modules may be configured receive a pulse sequence selection or configuration from a user input, and may control the two or more electrical current pulse sequences according to the user selection. The SNMR acquisition modules may be configured to send control signals to the various devices illustrated in FIG. 1 to control pulse sequence transmission.

In some embodiments, the SNMR acquisition modules may also be configured to control receiving and recording signal data received in response to transmitted pulse sequences. For example, the SNMR acquisition modules may be configured to operate receive switches 160, to place the acquisition system 100 in a receive mode to detect signals on the induction coils after and/or during each of the electrical current pulse sequences. Detected signals may be converted to signal data by the AD converter(s) 120, and the signal data may be recorded in a memory of the computing device 110 or elsewhere.

In some embodiments, SNMR processing modules may be configured to linearly combine detected signal data corresponding to separate electrical current pulse sequences to produce combined signal data in which one or more detected signal components are preserved and one or more different detected signal components are reduced or cancelled. The preserved signal components may comprise, for example, NMR signal data, such as desired NMR data, and the reduced or cancelled signal components may comprise undesired NMR signal data and/or non-NMR signal data. Alternatively, the preserved signal components comprise undesired NMR signal data and/or non-NMR signal data, the reduced or cancelled signal components comprise NMR signal data.

SNMR processing modules may be configured to process NMR data that is acquired according to the SNMR acquisition techniques discussed herein. For example, SNMR processing modules may be configured to identify NMR data corresponding to a plurality of different phase-shifted pulse sequences that correspond to a single NMR measurement, and to combine the identified NMR data. Similarly, SNMR processing modules may be configured to identify NMR data corresponding one or more specific pulses within a pulse sequence, and to combine such identified NMR data with NMR data from a corresponding, phase-shifted pulse from another pulse sequence. In some embodiments, the SNMR processing modules may be configured to preserve desired NMR signal data and cancel undesired NMR signal data. For example, SNMR processing modules may be configured to coherently combine detected NMR signals corresponding to separate electrical current pulse sequences to produce a combined NMR signal in which a desired FID signal is preserved, and undesired signals that are coherent with the timing of the electrical current pulse sequences but independent of the phases of the oscillating electrical current pulses are cancelled. Embodiments configured for the opposite operation are also possible, namely cancelling desired NMR signal data and preserving undesired NMR signal data. In some embodiments, SNMR processing modules may also be configured to perform additional processing operations, such as applying linear spatial inversion processing, non-linear spatial inversion processing, or correlation-based spatial processing, to localize detected NMR signals from underground liquids.

In some embodiments, multiple pulse sequences transmitted by an SNMR system 100 may be associated with a single SNMR measurement. For example, the pulse sequences may be designed to produce NMR data that is combined into a combined data set. The combined data set represents the end product of the single SNMR measurement, wherein the single SNMR measurement is obtained using a plurality of SNMR pulse sequences. NMR signal data from a plurality of SNMR pulse sequences may be combined according to SNMR processing techniques disclosed herein.

In some embodiments, each of the transmitted pulse sequences may comprise one or more oscillating electrical current pulses, and each of the oscillating electrical current pulses has a phase of oscillation relative to the other oscillating electrical current pulses in the two or more electrical current pulse sequences. For example, a phase of a second, third, or any subsequent pulse in a first pulse sequence may have a same phase of oscillation as a first pulse in the pulse sequence, or may be phase shifted by any amount between 0 and 360 degrees, relative to the first pulse. Similarly, a first, second, or any subsequent pulse in a second, third, or any subsequent pulse sequence may be phase shifted by any amount between 0 and 360 degrees, relative to a pulse in the first pulse sequence.

In some embodiments, the SNMR acquisition modules may be configured to apply phase shift(s) to the transmitted oscillating electrical current pulses in the transmitted pulse sequences. The SNMR acquisition modules may be configured to apply the phase shift by switching an AC voltage/current generator 130 input between different oscillating waveforms. In some embodiments, oscillating waveforms may be provided by oscillating waveform generator devices. The oscillating waveform generator devices may comprise, for example, function generators such as 111 and 112. Another example of oscillating waveform generator devices includes a computer, e.g., computer 110, equipped with waveform generating software and a DA signal converter. For example, the SNMR acquisition modules may either include or access waveform generating software that produces digital waveform(s), which are converted to analog waveform(s) by the DA signal converter. The SNMR acquisition modules may apply the phase shift by switching an AC voltage/current generator 130 input between oscillating waveforms produced by the waveform generating software.

In some embodiments, the phase shift applied by the SNMR acquisition modules may be relative to a phase of at least one of the transmitted oscillating electrical current pulses in another of the transmitted pulse sequences. Example pulse sequence configurations are discussed below.

In some pulse sequence configurations at least two transmitted electrical current pulse sequences may be applied, each pulse sequence consisting of a single oscillating electrical current pulse. The phase of a single oscillating electrical current pulse applied in at least one of the single pulse sequences may differ by substantially 180 degrees from the phase of a single oscillating electrical current pulse applied in at least another of the single pulse sequences. This approach may be referred to herein as FID phase cycling to suppress signals with constant envelope and phase functions, or "FID phase cycling".

In some embodiments, a FID phase cycling pulse sequence consisting of a single uninterrupted transmit pulse may be applied twice. In the second application of the pulse sequence, the phase of the transmit pulse may be shifted by substantially 180 degrees (also referred to as a phase shift of "pi") with respect to the phase of the transmit pulse in the first application of the pulse sequence. Each single pulse sequence may be followed by detection and recording of the resultant desired FID signal.

SNMR processing modules may be configured to process the data sets from the two applied FID phase cycling sequences, e.g. by coherently subtracting the data sets, yielding a single linearly combined data set. Since the phase of the NMR FID signal tracks the phase of the transmitted pulse, in the linearly combined data set the desired NMR FID signals add constructively and are hence preserved. Any instrumentation related artifact signals that are the same for the two applied signals, including electronic switching transients that are independent of the transmitted pulse phase, will be cancelled to zero in the linearly combined data set.

In some pulse sequence configurations, at least two transmitted electrical current pulse sequences may be applied, wherein at least two of the transmitted electrical current pulse sequences each consist of N oscillating electrical current pulses, wherein N is greater than one, and wherein each of the pulse sequences are separated by a time delay. The phase of any $i^{th}$ oscillating electrical current pulse applied in at least one of the N-pulse pulse sequences may differ by substantially 180 degrees from the phase of an $i^{th}$ oscillating electrical current pulse applied in at least another of the N-pulse pulse sequences. Some examples of this arrangement are provided below.

Regarding the time delay between pulses, a time delay separating the oscillating electrical current pulses in each of the pulse sequences may for example comprise a time delay that is shorter than the time for an underground liquid to achieve substantially complete longitudinal and/or transverse relaxation. Relaxation is an asymptotic process and therefore "complete relaxation" may be difficult to assess, and so a relaxation amounting to a substantially complete relaxation may be, e.g., a 75% or greater relaxation level.

In some pulse sequence configurations, at least two transmitted electrical current pulse sequences may be applied, each pulse sequence consisting of two oscillating electrical current pulses. The phase of a first oscillating electrical current pulse applied in at least one of the two-pulse pulse sequences may differ by substantially 180 degrees from the phase of a first oscillating electrical current pulse applied in at least another of the two-pulse pulse sequences.

A pulse sequence configuration using two oscillating electrical pulses, in which phase cycling can be applied, is referred to herein as pseudo-saturation-recovery phase cycled pulse sequence or "pseudo-saturation-recovery". A pseudo-saturation-recovery pulse sequence may comprise the transmission of two successive pulses of approximately the same pulse moment or transmitted energy, wherein the two pulses are separated by a time delay that is less than the time required for the targeted NMR processes to achieve complete longitudinal relaxation. In one embodiment of the pseudo-saturation-recovery sequence, the phase of the second pulse in the two-pulse sequence may be shifted by substantially 180 degrees with respect to the phase of the first pulse, in an attempt to limit the influence of non-uniform tip angles. In this SNMR pulse sequence, the desired NMR signals are the FID signals resulting from the action of the first and second pulses on the longitudinal magnetization state immediately prior to the pulse. The produced data are useful for estimating the abundance of subsurface liquids and also the T2* and/or T1 relaxation processes of the detected subsurface fluids.

In some embodiments, pseudo-saturation-recovery phase cycling may be applied to a two pulse sequence to preserve desired FID signals after the first and/or second pulse, and cancel or reduce undesired signals that exhibit a constant phase. Such undesired signals may include instrumentation or electronics-related transient signals that exhibit a signal or response that is independent of the transmitted pulse. A pseudo-saturation-recovery pulse sequence may consist of two uninterrupted transmit pulses, with a finite delay between the two pulses, wherein the transmitted energies of the first and second pulses may be approximately equal or different, and NMR signal acquisition may occur after the first and/or second pulses. The phase shift between the first and second pulses may be arbitrary. This two-pulse sequence may be applied twice. In the second application of the two-pulse sequence, the phase of first transmitted pulse may be shifted by substantially 180 degrees with respect to the phase of the first transmitted pulse in the first application of the sequence, and phase of the second transmitted pulse may be shifted by substantially 180 degrees with respect to the phase of the second transmitted pulse in the first application of the sequence. Each two-pulse sequence may be followed by detection and recording of the resultant desired FID signal.

SNMR processing modules may be configured to process the data sets from the pseudo-saturation-recovery type acquisition. The data sets from the two applied sequences may be subtracted, yielding a single linearly combined data set. Since the phase of the NMR FID signals tracks the phase of the transmitted pulses, in the linearly combined data set the desired NMR FID signals add constructively and are hence preserved. Any undesired signals that are the same for the two applied signals, including electronic switching transients that are independent of the transmitted pulse phase, will be cancelled to zero in the linearly combined data set.

In some pulse sequence configurations, at least four transmitted electrical current pulse sequences may be applied, each pulse sequence consisting of two oscillating electrical current pulses. Each of the four two-pulse pulse sequences may comprise a first oscillating electrical current pulse with a first phase, and a second oscillating electrical current pulse with a second phase. In one of the four two-pulse pulse sequences, the first phase and second phase may be substantially both at a same defined phase. In another of the four two-pulse pulse sequences, the first phase may be substantially the defined phase, and second phase may be shifted substantially 180 degrees from the defined phase. In another of the four two-pulse pulse sequences, the first phase may be shifted substantially 180 degrees from the defined phase, and second phase may be substantially the defined phase. In another of the four two-pulse pulse sequences, the first phase may be shifted substantially 180 degrees from the defined phase, and second phase may be shifted substantially 180 degrees from the defined phase. This approach may be referred to herein as 4-step pseudo-saturation-recovery phase cycling to suppress signals with constant envelope and phase, and remnant FID signals from the first and second pulses, or "4-step pseudo-saturation-recovery".

In some embodiments, a 4-step phase cycling pulse sequence may apply four two-pulse sequences to preserve desired FID signals after the first and/or second pulse, and cancel or reduce undesired signals that exhibit a constant phase. Such undesired signals may include instrumentation or electronics-related transient signals that exhibit a signal or response that is independent of the transmitted pulse. In addition, a separate linear combination of the acquired data may preserve the desired FID initiated by the second pulse while simultaneously canceling and remnant and overlapping portion of the FID signal initiated by the first pulse.

In some embodiments, a 4-step phase cycling pulse sequence may consist of two uninterrupted transmit pulses, with a finite delay between the two pulses, where in the transmitted energies of the first and second pulses may be approximately equal or different. NMR signal acquisition may occur after the first and/or second pulses. This two-pulse sequence may be applied four times. In the first application of the two-pulse sequence, the transmitted phases of the first and second pulses may be substantially identical. In the second application of the two-pulse sequence, the phase of first transmitted pulse may be shifted by substantially 180 degrees with respect to the phase of the first transmitted pulse in the first application of the sequence. In the third application of the two-pulse sequence, the phase of second transmitted pulse may be shifted by substantially 180 degrees with respect to the phase of the second transmitted pulse in the first application of the sequence. In the fourth application of the two-pulse sequence, the phase of first transmitted pulse may be shifted by substantially 180 degrees with respect to the phase of the first transmitted pulse in the first application of the sequence, and phase of second transmitted pulse may be shifted by substantially 180 degrees with respect to the phase of the second transmitted pulse in the first application of the sequence. Four sets of data may be received and recorded, and the relative phase shifts of the first FID signal $\phi_{FID1}$ and second FID signal $\phi_{FID2}$ for each data set for each data set, denoted as $(\phi_{FID1}, \phi_{FID2})$ may be as follows: A1=(0, 0), A2=(pi, 0), A3=(0, pi), A4=(pi, pi). The order in which the four sequences are acquired is arbitrary. On sequence A1, the phase of the first transmit pulse relative to the second transmit pulse is also arbitrary.

SNMR processing modules may be configured to process the data sets from 4-step pseudo-saturation-recovery by linearly combining the four sets of data in different ways to isolate different desired and/or undesired signals. For example, in a first linear combination C1, the fourth data set A4=(pi, pi) may be subtracted from the first data set A1=(0, 0) to yield a single combined data set in which the FID signals initiated by the first and second transmit pulses are preserved with zero phase shift C1=(0, 0), and any undesired signals with constant envelope and phase including instrumentation transients may be canceled or reduced.

In a second combination C2, the second data set A2=(pi, 0) may be subtracted from the third data set A3=(0, pi) to yield a single combined data set in which the FID signals initiated by the first and second transmit pulses are preserved with phase shifts C2=(0, pi), and any undesired signals with constant envelope and phase including instrumentation transients are canceled or reduced.

In a third combination C3, the third data set A3=(0, pi) may be subtracted from the first data set A1=(0, 0) to yield a single combined data set in which the FID signal initiated by the second transmit pulse is preserved with a phase of 0 degrees, and any undesired signals with constant envelope and phase following the second pulse, including instrumentation artifacts and/or any remnant FID signal initiated by the first pulse, may be canceled or reduced. This result is denoted C3=(X, 0), wherein the "X" indicated that the first FID signal has been cancelled, and the phase of the combined second FID signal is zero.

In a fourth combination C4, the second data set A2=(pi, 0) may be subtracted from the fourth data set A4=(pi, pi) to yield a single combined data set in which the FID signal initiated by the second transmit pulse is preserved with a phase shift of pi, and any undesired signals with constant envelope and phase following the second pulse, including instrumentation artifacts and/or any remnant FID signal initiated by the first pulse, may be canceled or reduced. This result is denoted C4=(X, pi), wherein the "X" indicated that the first FID signal has been cancelled, and the phase of the combined second FID signal is pi.

In a fifth combination C5, the second data set A2=(pi, 0) may be subtracted from the first data set A1=(0, 0) to yield a single combined data set in which the FID signal initiated by the first transmit pulse is preserved with a phase shift of 0, and any undesired signals with constant envelope and phase following the second pulse, including instrumentation artifacts and/or any remnant FID signal initiated by a previous application of the second pulse, may be canceled or reduced. This result is denoted C5=(0, X), wherein the "X" indicated that the second FID signal has been cancelled, and the phase of the combined first FID signal is 0.

In a sixth combination C6, the fourth data set A4=(pi, pi) may be subtracted from the third data set A3=(0, pi) to yield a single combined data set in which the FID signal initiated by the first transmit pulse is preserved with a phase shift of pi, and any undesired signals with constant envelope and phase following the second pulse, including instrumentation artifacts and/or any remnant FID signal initiated by a previous application of the second pulse, may be canceled or reduced. This result is denoted C6=(pi, X), wherein the "X" indicated that the second FID signal has been cancelled, and the phase of the combined first FID signal is pi.

Additional linear combinations of the acquired data may be formulated so as to preserve and/or suppress other specific desired NMR signals and/or instrumentation artifacts. For example, in a seventh combination C7 the first data set A1=(0, 0) may be added to the fourth data set A4=(pi, pi) to yield a single combined data set in which the FID signal initiated by the first transmit and second transmit pulses are canceled, and any non-NMR signals with constant envelope including instrumentation artifacts, are preserved. Similarly, in an eighth combination C8 the second data set A2=(pi, 0) may be added to the third data set A3=(0, pi) to yield a single combined data set in which the FID signal initiated by the first transmit and second transmit pulses are canceled, and any non-NMR signals with constant envelope including instrumentation artifacts, are preserved. The combinations C7 and C8 are useful for characterizing the non-NMR transient responses that may be related to instrumentation or other geophysical phenomena.

The first six linear combinations described above yield six combinations of the desired FID signals while undesired instrumentation artifacts and other undesired signals with constant envelope and phase are canceled or reduced: C1=(0, 0), C2=(0, pi), C3=(X, 0), C4=(X, pi), C5=(0, X), C6=(pi, X). These six linear combinations {C1, C2, C3, C4, C5, C6} may also be linearly combined in different ways to further enhance one or both of the desired FID signals. For example, the combinations C1 and C2 may be further combined via the equation D1=(C1+C2)/2, such that the first FID signal is preserved with zero phase shift and white Gaussian measurement noise is reduced by a factor of sqrt(2). Similarly the combinations C3 and C4 may be further combined via the equation D2=(C3−C4)/2, such that the second FID signal is preserved with zero phase shift, any remnant FID signal initiated by the first pulse is cancelled, and white Gaussian measurement noise is reduced by a factor of sqrt(2).

Additional combinations of the acquired data (A1, A2, A3, A4) and/or linear combinations of the acquired data (C1, C2, etc. . . . ) may be developed and applied to enhance other desired NMR signal processes or non-NMR signals of interest, and suppress specific undesired NMR and non-NMR signals.

Another pulse sequence configuration using two oscillating electrical pulses, in which phase cycling can be applied, is referred to herein as spin-echo phase cycled pulse sequence or "spin-echo". The spin-echo pulse sequences may comprise an oscillating electrical current excitation pulse, followed by a time delay, followed by an oscillating electrical current refocusing pulse. NMR signal acquisition may occur after the first and/or second pulses. The phase of an oscillating electrical current excitation pulse applied in at least one of the spin-echo pulse sequences may differ by substantially 180 degrees from the phase of an oscillating electrical current excitation pulse applied in at least another of the spin-echo pulse sequences. This approach may be referred to herein as spin echo phase cycling to isolate spin echoes from FID signals or "spin echo".

In some embodiments, a spin echo pulse sequence may comprise two pulses that may have different duration or amplitude, and may be transmitted in succession separated by a delay time. The initial pulse acts to rotate a component of the magnetization from the longitudinal plane into the transverse plane. The magnetization signal in the transverse plane produced by this pulse decays over time as the magnetization loses phase coherence in an inhomogeneous background field. The second pulse, called the refocusing pulse, applied after a delay time alters the magnetization state and causes a portion of the transverse magnetization to refocus, forming a so-called spin echo signal, centered in time at approximately twice the delay time. The amplitude of the echo signal is a function of the delay time and the relaxation time T2. By repeating the measurement using different delay times it is possible to determine T2.

The refocusing pulse may not only create the spin echo signal, but also other undesired NMR signals. This is especially true in SNMR measurements where the transmitted B1 field can vary widely over the detectable depth range in a near surface aquifer. In addition to refocusing a portion of the transverse magnetization from the first pulse to form an echo signal, the second pulse can also rotate new magnetization from the longitudinal axis into the transverse plane, creating a secondary transverse magnetization FID signal. The secondary transverse magnetization FID signal may overlap and interfere (constructively or deconstructively) with the desired spin echo signal.

Figure 5:
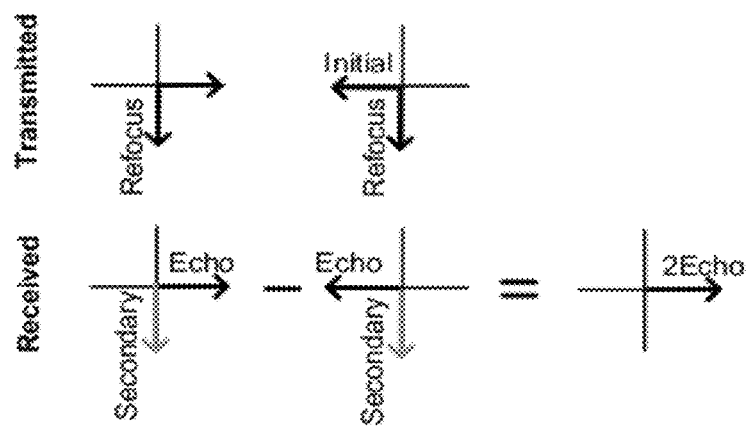
FIG. 5 illustrates example transmitted pulses comprising excitation pulses and refocusing pulses, in the top graphs, that produce signals illustrated in the bottom graphs, which may be recorded and combined as shown.

The phase of the secondary transverse magnetization signal, on the other hand, will be correlated with the phase of the refocusing pulse and independent of the phase of the initial pulse. Thus maintaining a constant phase ø for the refocusing pulse, and cycling the phase of the initial pulse (e.g. between ø+90° and ø−90° in a pair of measurements), will likewise cycle the phase of the echo signal by 180 degrees between measurements. The secondary transverse magnetization signal and other signals which do not depend on the phase of the initial transmit pulse will be unaffected by the phase cycling and will maintain constant phase for both measurements. Thus using a method such as illustrated in FIG. 5, in which the phase of the excitation pulse is cycled between ø+90 and ø−90 and the refocusing pulse has a fixed phase of ø, as shown in the two top graphs, provides two recorded signals pairs, shown at bottom left and bottom middle, which can be subtracted to isolate the echo signal from the secondary transverse magnetization signal, as shown in the bottom right graph.

In some embodiments, a spin echo pulse sequence may comprise the transmission of a first pulse, followed by a time delay that is not long in comparison to the transverse relaxation time (T2) for the NMR process of interest, followed by a second transmitted pulse which has a pulse moment approximately twice that of the first pulse, followed by detection of a delayed and desired spin echo signal. In some embodiments of the spin echo pulse sequence with phase cycling, the phase of the second pulse in the two-pulse sequence may be shifted by 90 degrees or 180 degrees with respect to the phase of the first pulse.

In some embodiments, a two-pulse spin echo sequence may be applied to preserve the desired spin echo signals after each refocusing pulse, and cancel undesired signals that exhibit a constant phase. Such undesired signals may include instrumentation or electronics-related transient signals that exhibit a signal or response that is independent of the transmitted pulse, and/or FID NMR signals initiated by the excitation or refocusing pulses. For example, a spin echo pulse sequence may consist of an excitation transmit pulse, followed by a finite time delay, followed by a refocusing pulse wherein NMR signal acquisition may occur after the excitation and/or refocusing pulses. The transmitted energy of the refocusing pulse may be arbitrary relative to that of the excitation pulse, or may be twice that of the excitation pulse. The phase shift between the excitation and refocusing pulses may be arbitrary. This two-pulse sequence may be applied twice. In the second application of the two-pulse sequence, the phase of first transmitted pulse may be shifted by substantially 180 degrees with respect to the phase of the first transmitted pulse in the first application of the sequence. Each two-pulse sequence may be followed by detection and recording of the resultant NMR signal.

SNMR processing modules may be configured to process the data sets from the two applied spin echo sequences, e.g. by subtracting the data sets, yielding one linearly combined data set. Since the phase of the NMR spin echo signal tracks the phase of the excitation pulse, and may be shifted by substantially 180 degrees in the two individual data sets, in the linearly combined data set the desired NMR spin echo signals add constructively and are hence preserved. Any undesired signals that are the same for the two applied signals including electronic switching transients that are independent of the transmitted pulse phase, transient signals from eddy currents associated with rapid termination of the refocusing pulse, and/or any FID signals initiated by the refocusing pulse may be cancelled to zero in the linearly combined data set.

In some embodiments, SNMR processing modules may be configured to process a linearly combined dataset, in which the echo signals are preserved, to estimate the localized NMR relaxation parameters T2* and/or T2.

In some embodiments, SNMR processing modules may be configured to process a linearly combined data set by adding, rather than subtracting, the datasets from the two applied spin echo sequences. In such a linearly combined dataset, the spin echo signals are cancelled and the FID signals initiated by the refocusing pulses are preserved because the FID signals initiated by the refocusing pulse have consistent phase in the two individual data sets and so add constructively and are hence preserved. SNMR processing modules may be configured to use a linearly combined dataset, in which the FID signals initiated by the refocusing pulse are preserved, to estimate the localized NMR relaxation parameters T1 and/or T2*.

In some embodiments, spin echo acquisition may comprise 4-step spin echo phase cycling to isolate the spin echoes signals as well as FID signals from the first pulse and refocusing pulse, or "4-step spin echo". In a 4-step spin echo acquisition the two-pulse spin echo sequence may be applied four times with similar cycling of transmitted pulse phases as described previously for the 4-step pseudo saturation-recovery. In the first application of the two-pulse sequence, the transmitted phases of the first and second pulses may be arbitrary. In the second application of the two-pulse sequence, the phase of first transmitted pulse may be shifted by substantially 180 degrees with respect to the phase of the first transmitted pulse in the first application of the sequence. In the third application of the two-pulse sequence, the phase of second transmitted pulse may be shifted by substantially 180 degrees with respect to the phase of the second transmitted pulse in the first application of the sequence. In the fourth application of the two-pulse sequence, the phase of first transmitted pulse may be shifted by substantially 180 degrees with respect to the phase of the first transmitted pulse in the first application of the sequence, and phase of second transmitted pulse may be shifted by substantially 180 degrees with respect to the phase of the second transmitted pulse in the first application of the sequence. Four sets of data may be received and recorded, and the relative phase shifts of the second FID signal $\phi_{FID2}$ and second FID signal $\phi_{ECHO}$ for each data set for each data set, denoted as ($\phi_{FID1}$, $\phi_{FID2}$, $\phi_{ECHO}$) may be as follows: A1=(0, 0, 0), A2=(pi, 0, pi), A3=(0, pi, 0), A4=(pi, pi, pi). The order in which the four sequences are acquired is arbitrary. On sequence A1, the phase of the first transmit pulse relative to the second transmit pulse is also arbitrary.

SNMR processing modules may be configured to process the data sets from 4-step pseudo-saturation-recovery by linearly combining the four sets of data in different ways to isolate different desired and/or undesired signals. For example, in a first linear combination C1, the second data set A2=(pi, 0, pi) may be subtracted from the first data set A1=(0, 0, 0) to yield a single combined data set in which the spin echo signals and first FID signals are preserved with zero phase shift, and any undesired signals with constant envelope and phase including the FID from the second pulse may be canceled or reduced. This result is denoted C1=(0, X, 0), wherein the "X" indicated that the second FID signal has been cancelled, and the phase of the combined first FID signal and spin echo signal are zero.

In a second combination C2, the third data set A3=(0, pi, 0) may be subtracted from the fourth data set A4=(pi, pi, pi) to yield another single combined data set, C2=(pi, X, pi), in which the spin echo signals and first FID signals are preserved with zero phase shift and any undesired signals with constant envelope and phase including the FID from the second pulse may be canceled or reduced.

In a third combination C3, the third data set A3=(0, pi, 0) may be subtracted from the first data set A1=(0, 0, 0) to yield a single combined data set in which the FID signal initiated by the second transmit pulse is preserved with a phase of 0 degrees, and any undesired signals with constant envelope and phase following the second pulse, including instrumentation artifacts, spin echo signals, and/or any remnant FID signal initiated by the first pulse, may be canceled or reduced. This result is denoted C3=(X, 0, X), wherein the "X" indicated that the first FID signal as well as any echo signals have been cancelled, and the phase of the combined second FID signal is zero.

In a fourth combination C4, the second data set A2=(pi, 0, pi) may be subtracted from the fourth data set A4=(pi, pi, pi) to yield a single combined data set, C4=(X, pi, X), in which the FID signal initiated by the second transmit pulse is preserved with a phase shift of pi, and any undesired signals with constant envelope and phase following the second pulse, including instrumentation artifacts, spin echo signals, and/or any remnant FID signal initiated by the first pulse, may be canceled or reduced.

In a fifth combination C5, the fourth data set A4=(pi, pi, pi) may be subtracted from the first data set A1=(0, 0, 0) to yield a single combined data set in which the FID signal initiated by the first transmit pulse, the FID signal initiated by the second pulse and the spin echo signal are all preserved with a phase shift of 0, and any undesired signals with constant envelope and phase following the second pulse, including instrumentation artifacts may be canceled or reduced. This result is denoted C5=(0, 0, 0).

In a sixth combination C6, the third data set A3=(0, pi, 0) may be subtracted from the second data set A2=(pi, 0, pi) to yield a single combined data set in which the FID signal initiated by the first transmit pulse and the spin echo signal are both preserved with a phase shift of pi, the FID signal initiated by the second pulse is preserved with a phase shift of 0, and any undesired signals with constant envelope and phase, including instrumentation, may be canceled or reduced. This result is denoted C6=(pi, 0, pi).

The first six linear combinations described above yield six combinations of the desired FID signals while undesired instrumentation artifacts and other undesired signals with constant envelope and phase are canceled or reduced: C1=(0, X, 0), C2=(pi, X, pi), C3=(X, 0, X), C4=(X, pi, X), C5=(0, 0, 0), C6=(pi, 0, pi). These six linear combinations {C1, C2, C3, C4, C5, C6} may also be linearly combined in different ways to further enhance one or both of the desired FID signals. For example, the combinations C1 and C2 may be further combined via the equation D1=(C1−C2)/2, such that the first FID signal and spin echo signal are preserved with zero phase shift and white Gaussian measurement noise is reduced by a factor of sqrt(2). Similarly the combinations C3 and C4 may be further combined via the equation D2=(C3−C4)/2, such that the second FID signal is preserved with zero phase shift, any remnant FID signal initiated by the first pulse or spin echo signals are cancelled, and white Gaussian measurement noise is reduced by a factor of sqrt(2).

Additional combinations of the acquired data (A1, A2, A3, A4) and/or linear combinations of the acquired data (C1, C2, etc. . . . ) may be developed and applied to enhance other desired NMR signal processes or non-NMR signals of interest, and suppress specific undesired NMR and non-NMR signals.

The aforementioned embodiments of the phase-cycled pseudo saturation recovery and the phase-cycled spin echo use similar phase variations for the transmitted pulses. The primary deference between the two acquisition methods is the amplitude of transmitted energy of the second pulse relative to the first pulse. In some embodiments of the pseudo saturation recovery sequence, the transmitted energy of the second pulse may be approximately equal to that of the first pulse. In some embodiments of the spin echo sequence, the transmitted energy of the second pulse may be approximately twice that of the first pulse. In other embodiments, the same general 4-step phase cycling approach may be used for a general acquisition scheme in which the transmitted energy of the second pulse may be arbitrary relative to that of the first pulse. Data produced from such embodiments, in which the transmitted energy of the two pulses is arbitrary, can also be used to record and isolate FID and spin echo signals and to localize and estimate the abundance of subsurface fluids and also the T2* and/or T1 relaxation processes of the detected subsurface fluids.

In some pulse sequence configurations, at least two transmitted electrical current pulse sequences may each comprise a Carr-Purcell-Meiboom-Gill (CPMG) pulse sequence. The Carr-Purcell-Meiboom-Gill (CPMG) pulse sequences may comprise an oscillating electrical current excitation pulse, followed by a series of one or more time delays and oscillating electrical current refocusing pulses, each refocusing pulse having a pulse moment approximately twice as large as the excitation pulse, and each refocusing pulse having a phase substantially equal to the phase of the other refocusing pulses within a same pulse sequence. The phase of either an oscillating electrical current excitation pulse, or the refocusing pulses applied in at least one of the CPMG pulse sequences may differ by substantially 180 degrees from the phase of an oscillating electrical current excitation pulse, or the refocusing pulses, respectively, applied in at least another of the CPMG pulse sequences. This approach may be referred to herein as phase cycled CPMG acquisition.

In some embodiments, a phase cycled CPMG pulse sequence may comprise the application of a first pulse with finite energy, followed by a predetermined time delay, followed by a set of refocusing pulses, each of said refocusing pulses having energy approximately twice that of the first pulse, and wherein each of the refocusing pulses are separated by time delays equal to twice the initial delay period. The CPMG pulse sequence causes NMR spin echo signals to refocus in the time intervals approximately midway between each of the refocusing pulses. The CPMG sequence is useful for estimating the abundance of subsurface fluid and its distribution in different T2 relaxation times.

In some embodiments, a phase cycled CPMG pulse sequence may comprise a first transmitted pulse (excitation pulse) is applied to generate a transverse magnetization, followed by a plurality of time delays and refocusing pulses, where each refocusing pulse has a substantially identical transmit phase. The transmitted energy of the individual refocusing pulses may be arbitrary, or may be twice as large as that of the first transmitted excitation pulse. In this embodiment, two separate CPMG acquisitions may be performed, wherein the phase of the excitation pulse in the second acquisition is shifted by substantially 180 degrees relative to the phase of the excitation pulse in the first acquisition. Each CPMG pulse sequence may be followed by detection and recording of the resultant desired FID signal.

SNMR processing modules may be configured to process the data sets from the CPMG pulse sequences. Recorded NMR signal data from the second acquisition may be coherently subtracted from the NMR signal data from the first acquisition, to produce a final NMR signal. In this final NMR signal, the desired spin echo NMR signals are preserved, and any undesired signals that are coherent with the timing of the acquisitions but independent of the transmitted pulse phases are cancelled. In addition, in the final NMR signal any additional undesired NMR signals that are in phase with the refocusing pulses, including spurious FID signals generated by the refocusing pulses, are cancelled.

Figure 3:
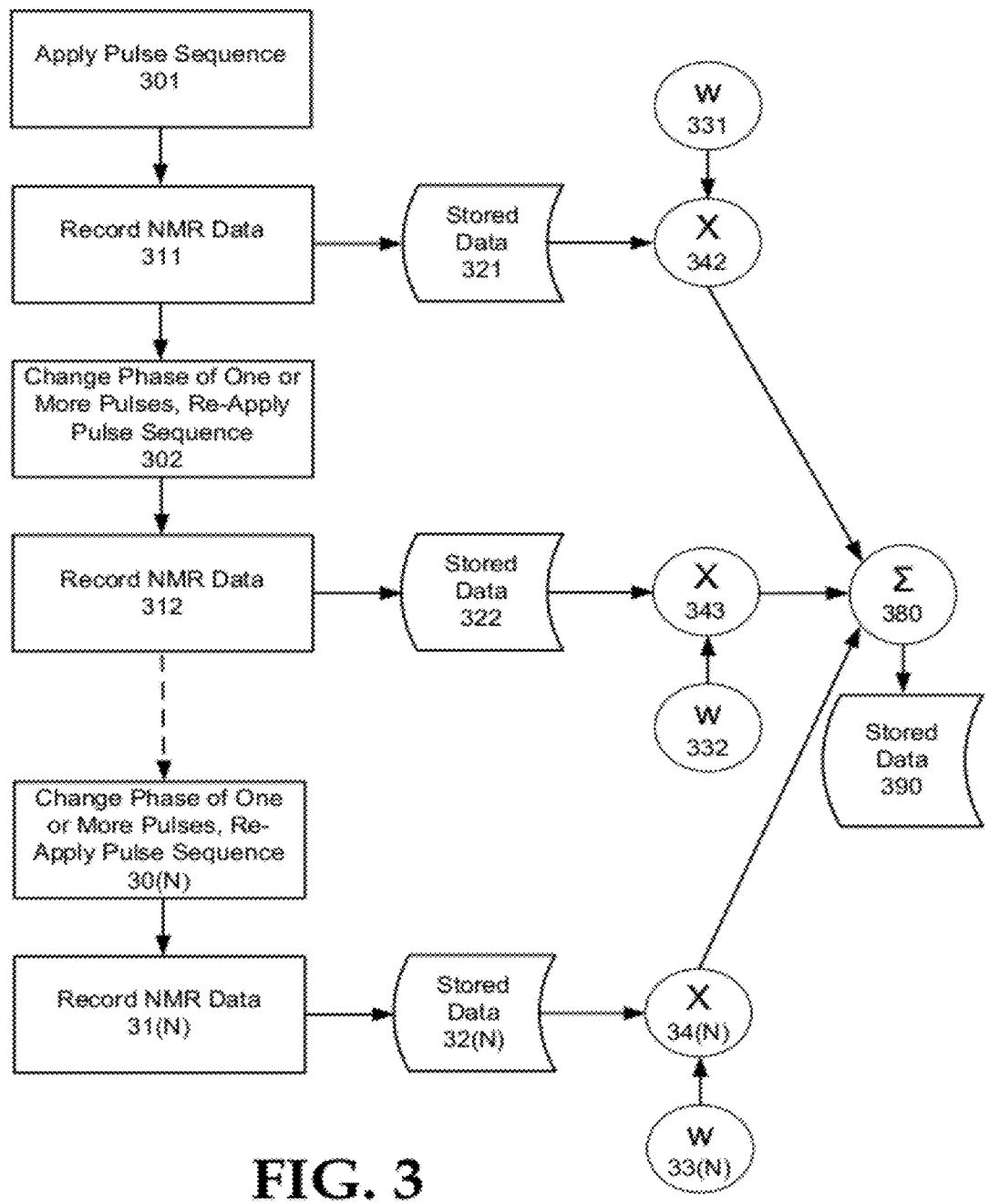
FIG. 3 is a flow diagram illustrating example SNMR pulse sequence phase cycling methods.

FIG. 3 is a flow diagram illustrating example SNMR pulse sequence phase cycling methods. The various elements illustrated in FIG. 3 illustrate both operations that may be performed in a method, and modules as may be included in a computing device 110. These include an "Apply Pulse Sequence" block 301, a "Record NMR Data" block 311, a "Change Phase of One or More Pulses, and Re-Apply Pulse Sequence" block 302, a "Record NMR Data" block 312, a "Change Phase of One or More Pulses, and Re-Apply Pulse Sequence" block 30(N), a "Record NMR Data" block 31(N).

In FIG. 3, operations 302 and 312 may be repeated N times, where N can be any number from zero to any desired number of repetitions. Each of the "Record NMR Data" blocks 311, 312, 31(N) produce stored data 321, 322, and 32(N), respectively. The stored data is processed for example by multipliers 342, 343, and 34(N), which multiply by the real or complex scalars 331, 332, and 33(N). The output of the multipliers 342, 343, and 34(N) may be summed by summing operator 380, which produces stored data output 390.

In some embodiments according to FIG. 3, a phase cycled SNMR data acquisition and recombination set may consist of two phase cycles, e.g., two pulse sequences in which the phase of one or more pulses in the second pulse sequence is different from a phase of a corresponding pulse in the first pulse sequence. A first SNMR pulse sequence is applied 301, resulting in the recording 311 and storage of a first data set 321. The phase of one or more of the pulses in the pulse sequence 301 is changed and the pulse sequence is reapplied 302 resulting in the recording 312 and storage of a second data set 322. The relative phases of the desired NMR signal and undesired signal(s) are different in the two data sets 321 and 322, due to the change of the phase in the one or more transmit pulses between the first pulse sequence 301 and second pulse sequence 302. The two data sets 321 and 322, may be linearly combined into a single data set via multiplication 342 and 343 by the real or complex scalars 331 and 332, and subsequent summation 380. In the combined and stored data set 390, a desired NMR signal is preserved and one or more undesired signals(s) are canceled or reduced.

In some embodiments according to FIG. 3, a phase cycled SNMR data acquisition and recombination set may comprise more than two phase cycles, e.g., more than two pulse sequences in which the phase of one or more pulses in at least one of the subsequent pulse sequences is different from a phase of a corresponding pulse in a previous pulse sequence. For example, a SNMR pulse sequence may be applied N times using N unique combinations of phases on the individual pulses in the pulse sequence (301, 302, 30(N)), resulting in the recording (311, 312, 31(N)) and storage of N data sets (321, 322, 32(N)). The relative phases of the desired NMR signal and undesired signal(s) are different among the plurality of stored data sets (321, 322, 32(N)) due to the unique combinations of transmit pulse phases in the plurality of applications of the pulse sequence (301, 302, 30(N)). The N data sets (321, 322, 32(N)) may be linearly combined into a single data set via multiplication (342, 343, 34(N)) by the real or complex scalars (331, 332, 33(N)) and subsequent summation 380. In the combined and stored data set 390, a desired NMR signal is preserved and one or more undesired signals(s) are canceled or reduced.

In some embodiments, the operations illustrated in FIG. 3 may be separated into acquisition and processing, e.g., by first carrying out the acquisition of NMR data, then performing the processing either at a later time or with a different device. Also, the operations illustrated in FIG. 3 may be combined with any number of operations involved in performing SNMR measurements using a system such as illustrated in FIG. 1. For example, SNMR detection operations may generally comprise deploying one or more induction coils on or above the surface of the Earth for use as magnetic field transmitting sources and/or magnetic field detection devices, deploying one or more induction coils on or above the surface of the Earth for use as magnetic field detection devices, transmitting a sequence of one or more current pulses through one or more of the transmitting coils at or near the Larmor frequency of the Earth's local magnetic field, to cause a coherent precession of NMR spins in fluid(s) in the subsurface, and/or using the one or more detection coils to detect the alternating magnetic field caused by the precessing NMR spins in the subsurface fluid(s).

A single induction coil may be used for both transmitting and detection, or separate coils may be used for transmitting and detection functions. The SNMR detection methods disclosed herein may be employ multiple transmit and detection coils, for example as disclosed in U.S. Pat. No. 7,466,128. Various methods have been developed for localizing NMR signals acquired via SNMR detection techniques, and these localization methods have been applied to localize NMR signals in one, two or three dimensions. Various methods have also been developed and applied to estimate aquifer and reservoir properties based on NMR data obtained using the SNMR detection technique, and such methods may also be combined with the operations disclosed herein.

In some embodiments, the SNMR methods disclosed herein may be used to detect fluids beneath the surface of the Earth, including groundwater and hydrocarbon fluids. SNMR techniques may also applicable to detection of fluids beneath and within man-made structures, including earthen or concrete dams, levees, mine tailing piles, piles of raw or processed materials, and landfills. SNMR methods are also potentially useful for detecting fluids beneath the surfaces of extraterrestrial bodies, including nearby planets such as Mars. In the extraterrestrial application, the method would rely upon a local static magnetic field produced by the extraterrestrial body itself, rather than the Earth's magnetic field.

In some embodiments, SNMR methods may generally comprise the transmission of a specific sequence of pulses, to activate NMR signal processes in the Earth's magnetic field, and the simultaneous detection of desired NMR signals due to fluids in the subsurface. The SNMR detection method may thus produce data that is subsequently useful for analysis of distribution of fluid content in the subsurface.

In some embodiments, the SNMR methods disclosed herein may separate "desired" from "undesired" coherent signals. The desired signals are those particular coherent NMR signals emitted by subsurface liquids that can be analyzed to determine the NMR properties of the subsurface. The undesired signals are any coherent signals that interfere with the recording of the desired signal or the determination of subsurface NMR properties, and may include signals from non-NMR sources as well interfering signals from NMR sources. In particular, non-NMR sources of undesired signals may include transient responses of the SNMR detection apparatus that do not necessarily follow the amplitude and phase of the transmitted pulse(s). Sources of these types of non-NMR signals may include switching devices, transient responses of electrical circuits, or any other source of signal that is timed-locked with the SNMR detection sequence but not necessarily dependent on the transmitted pulse or pulses. Non-NMR sources of undesired signals may also include transient responses of the subsurface associated with eddy currents induced by the rapid shut-off of the transmitted pulse(s).

NMR-related sources of undesired signals may include remnant FID signals, and/or undesired stimulated or refocused NMR signals. For example in a spin-echo sequence, the application of the second pulse can generate a FID signal which can interfere with the detection and interpretation of the desired spin echo signal or signals. Also, in a pseudo-inversion-recovery sequence, the FID signal from the first pulse can overlap in time with the desired FID signal from the second pulse, thus interfering with detection and interpretation of the second pulse FID signal.

The various desired and undesired signal components may have similar spectral properties and may overlap in the time domain as well, so it is generally difficult to separate the desired signals from those which are undesired. In particular, the presence of undesired transient signals that are concentrated at the beginning of the recorded data can inhibit the ability to detect and interpret the desired early time NMR signals. The disclosed methods may be employed to robustly suppress the undesired signals and preserve the desired NMR signals that can be used to determine the NMR properties of the subsurface.

In some embodiments, the SNMR methods disclosed herein may comprise methods configured to acquire SNMR signals in a set of two or more repeated acquisition sequences, also referred to herein as pulse sequences, involving a phase shift on one or more of the transmitted pulses in one or more of the acquisition sequences. Disclosed methods may comprise, alternatively or in addition to the SNMR acquisition, SNMR processing including linearly combining the signals recorded during the two or more acquisition sequences so as to suppress an undesired signal or signals and to preserve a desired signal or signals. We define phase cycling as the process of performing two or more repeated SNMR measurements, wherein the phase of one or more of the pulses in the sequence is varied between the two or more repeated measurements. Embodiments of this disclosure can also be used to cancel or reduce one or more NMR signals for the purpose of detecting and isolating one or more non-NMR signals.

In some embodiments, a single acquisition sequence may comprise (1) transmitting one or more pulses in a sequence of short succession on one or more transmit coils (2) recording the voltage signal on one or more receive coils after one of more transmit pulses and (3) waiting a period of time after the final pulse in the sequence to allow the subsurface NMR state to return to equilibrium, which may be equal to or greater than the T1 relaxation process for the subsurface liquids of interest. A cycled set of sequences may be comprised of two or more similar acquisition sequences between which a controlled phase shift is applied to one or more transmit pulses.

In some embodiments, a SNMR detection sequence may be designed or selected so as to detect a desired NMR signal. One or more undesired signals or processes may be identified. A phase alternating set of acquisitions may be designed so as to preserve the desired NMR signal while canceling or reducing the undesired signal(s). The selected pulse sequence may be performed two or more times wherein the phase of at least one pulse in the selected sequence is varied between at least two of the performed pulse sequences, resulting in two or more data sets. The two or more data sets may be linearly combined into a single data set that preserves the desired NMR signal and cancels or reduces the one or more undesired signals.

In some embodiments, the process of collecting data in the aforementioned phase cycled manner, and recombining the phase cycled data, may employ any linear combination of the recorded data that causes a desired NMR signal to be preserved and one or more undesired signals to be canceled or reduced. In particular, the linear combination may involve subtracting one or more of the sampled data sets from other data sets or combinations thereof, phase shifting individual data sets via multiplication by complex scalar values and then performing addition or subtraction among various data sets, and linearly combining different samples in time.

There is little distinction left between hardware and software implementations of aspects of systems; the use of hardware or software is generally (but not always) a design choice representing cost vs. efficiency tradeoffs. There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A Surface Nuclear Magnetic Resonance (SNMR) method, comprising:
   arranging one or more induction coils on the surface of the Earth;
   transmitting two or more electrical current pulse sequences on the induction coils, wherein each of the transmitted pulse sequences are associated with a single NMR measurement, wherein each of the transmitted pulse sequences comprises one or more oscillating electrical current pulses, and wherein each of the oscillating electrical current pulses has a phase of oscillation relative to the other oscillating electrical current pulses in the two or more transmitted pulse sequences;
   applying a phase shift to at least one of the transmitted oscillating electrical current pulses in at least one of the transmitted pulse sequences, wherein the applied phase shift is relative to a phase of at least one of the transmitted oscillating electrical current pulses in another of the transmitted pulse sequences;
   detecting signals on the induction coils after and/or during each of the electrical current pulse sequences; and
   linearly combining detected signal data corresponding to separate electrical current pulse sequences to produce combined signal data in which one or more detected signal components are preserved and one or more different detected signal components are reduced or cancelled.

2. The SNMR method of claim 1, wherein the preserved signal components comprise NMR signal data, and wherein the reduced or cancelled signal components comprise one or more of undesired NMR signal data and non-NMR signal data.

3. The SNMR method of claim 1, wherein the preserved signal components comprise one or more of undesired NMR signal data and non-NMR signal data, and wherein the reduced or cancelled signal components comprise NMR signal data.

4. The SNMR method of claim 1:
   wherein at least two of the transmitted electrical current pulse sequences each consist of a single oscillating electrical current pulse; and
   wherein the phase of a single oscillating electrical current pulse applied in at least one of the single pulse sequences differs by substantially 180 degrees from the phase of a single oscillating electrical current pulse applied in at least another of the single pulse sequences.

5. The SNMR method of claim 1:
   wherein at least two of the transmitted electrical current pulse sequences each consist of two oscillating electrical current pulses separated by a time delay.

6. The SNMR method of claim 5:
   wherein the phase of the first oscillating electrical current pulse applied in at least one of the two-pulse pulse sequences differs by substantially 180 degrees from the phase of the second electrical current pulse applied in at least another of the two-pulse pulse sequences; or
   wherein the phase of the second oscillating electrical current pulse applied in at least one of the two-pulse pulse sequences differs by substantially 180 degrees from the phase of the second electrical current pulse applied in at least another of the two-pulse pulse sequences; or
   wherein the phase of the first and second oscillating electrical current pulses applied in at least one of the two-pulse pulse sequences each differ by substantially 180 degrees from the phase of the first and second electrical current pulses, respectively, applied in at least another of the two-pulse pulse sequences.

7. The SNMR method of claim 5:
   wherein at least four of the transmitted electrical current pulse sequences each consist of two oscillating electrical current pulses separated by a time delay;
   wherein each of the four two-pulse pulse sequences comprises a first oscillating electrical current pulse with a first phase, and a second oscillating electrical current pulse with a second phase;

wherein in one of the four two-pulse pulse sequences, the first phase is substantially at a defined reference first phase and second phase is substantially at a defined reference second phase;

wherein in another of the four two-pulse pulse sequences, the first phase is substantially at the defined reference first phase, and second phase is shifted substantially 180 degrees from the defined reference second phase;

wherein in another of the four two-pulse pulse sequences, the first phase is shifted substantially 180 degrees from the defined reference first phase, and second phase is substantially at the defined reference second phase; and wherein in another of the four two-pulse pulse sequences, the first phase is shifted substantially 180 degrees from the defined reference first phase, and second phase is shifted substantially 180 degrees from the defined reference second phase.

8. The SNMR method of claim 5, wherein at least two of the oscillating electrical current pulses in each of the pulse sequences is separated by a time delay that is shorter than the time for an underground liquid to achieve substantially complete longitudinal and/or transverse relaxation.

9. The SNMR method of claim 5,
wherein the oscillating electrical current pulses in the two-pulse pulse sequences have substantially equal moment; or
wherein the amplitude of the first oscillating electrical current pulse in the two-pulse sequence is substantially greater than the pulse moment of the second oscillating electrical current pulse; or
wherein the amplitude of the first oscillating electrical current pulse in the two-pulse sequence is substantially less than the pulse moment of the second oscillating electrical current pulse.

10. The SNMR method of claim 5, wherein at least two of the transmitted electrical current pulse sequences each comprise a spin-echo pulse sequence, the spin-echo pulse sequences comprising an oscillating electrical current excitation pulse, followed by a time delay, followed by an oscillating electrical current refocusing pulse; and
wherein the phase of an oscillating electrical current excitation pulse applied in at least one of the spin-echo pulse sequences differs by substantially 180 degrees from the phase of an oscillating electrical current excitation pulse applied in at least another of the spin-echo pulse sequences.

11. The SNMR method of claim 1:
wherein at least two of the transmitted electrical current pulse sequences each consist of N oscillating electrical current pulses, were N is greater than one, and wherein each of the pulse sequences are separated by a time delay; and
wherein the phase of any $i^{th}$ oscillating electrical current pulse applied in at least one of the N-pulse pulse sequences differs by substantially 180 degrees from the phase of an $i^{th}$ oscillating electrical current pulse applied in at least another of the N-pulse pulse sequences.

12. The SNMR method of claim 1:
wherein at least two of the transmitted electrical current pulse sequences each comprise a Carr-Purcell-Meiboom-Gill (CPMG) pulse sequence, the CPMG pulse sequences comprising an oscillating electrical current excitation pulse, followed by a series of one or more time delays and oscillating electrical current refocusing pulses, each refocusing pulse having a pulse moment approximately twice as large as the excitation pulse, and each refocusing pulse having a phase substantially equal to the phase of the other refocusing pulses within a same pulse sequence; and
wherein the phase of either an oscillating electrical current excitation pulse, or the refocusing pulses applied in at least one of the CPMG pulse sequences differs by substantially 180 degrees from the phase of an oscillating electrical current excitation pulse, or the refocusing pulses, respectively, applied in at least another of the CPMG pulse sequences.

13. The SNMR method of claim 1, wherein the oscillating electrical current excitation pulses generate a transverse nuclear magnetization in an underground liquid.

14. The SNMR method of claim 13, further comprising applying linear spatial inversion processing, non-linear spatial inversion processing, or correlation-based spatial processing, to localize detected NMR signals from underground liquids.

15. The SNMR method of claim 14, further comprising using the localized detected NMR signals to estimate underground fluid content and its spatial distribution.

16. The SNMR method of claim 15, further comprising using estimated underground fluid content and its spatial distribution to estimate properties of fluid-bearing underground formations, including groundwater aquifers and hydrocarbon reservoirs.

17. The SNMR method of claim 16, further comprising using the localized detected NMR signals to estimate localized NMR relaxation parameters comprising one or more of longitudinal relaxation T1, FID relaxation rate T2*, and/or spin-spin relaxation T2.

18. A Surface Nuclear Magnetic Resonance (SNMR) system configured to produce NMR in underground liquids, comprising:
a SNMR phase cycling computer comprising a processor and memory;
the SNMR phase cycling computer comprising one or more SNMR phase cycling acquisition modules configured to control transmitting of two or more electrical current pulse sequences on induction coils arrangeable on or above the surface of the Earth, wherein each of the transmitted pulse sequences are associated with a single NMR measurement, wherein each of the transmitted pulse sequences comprises one or more oscillating electrical current pulses, and wherein each of the oscillating electrical current pulses has a phase of oscillation relative to the other oscillating electrical current pulses in the two or more electrical current pulse sequences; and
one or more SNMR phase cycling acquisition modules configured to apply a phase shift to at least one of the transmitted oscillating electrical current pulses in at least one of the transmitted pulse sequences, wherein the applied phase shift is relative to a phase of at least one of the transmitted oscillating electrical current pulses in another of the transmitted pulse sequences.

19. The SNMR system of claim 18, wherein the computer is configured to control transmitting of two or more electrical current pulse sequences via a power amplifier coupled with the induction coils, and wherein the computer is configured to apply the phase shift by switching a power amplifier input between oscillating waveform generator devices.

20. The SNMR system of claim 19, wherein the oscillating waveform generator devices comprise one or more of a function generator and a waveform generating computer, wherein the waveform generating computer is equipped with waveform generating software and a digital to analog signal converter.

* * * * *